United States Patent [19]

Tihon et al.

[11] Patent Number: 5,415,656

[45] Date of Patent: May 16, 1995

[54] ELECTROSURGICAL APPARATUS

[75] Inventors: Claude Tihon, Hennepin; W. Scott Andrus, Eden Prairie; Ronald Svejkovsky, Hennepin, all of Minn.

[73] Assignee: American Medical Systems, Inc., Minnetonka, Minn.

[21] Appl. No.: 127,674

[22] Filed: Sep. 28, 1993

[51] Int. Cl.⁶ .............................................. A61B 17/39
[52] U.S. Cl. ................................... 606/46; 606/47
[58] Field of Search .................................. 606/46, 47

[56] References Cited

U.S. PATENT DOCUMENTS

| | | | |
|---|---|---|---|
| 3,910,279 | 10/1975 | Okada et al. | 606/47 |
| 4,011,872 | 3/1977 | Komiya | 606/47 |
| 4,638,802 | 1/1987 | Okada | 606/47 |
| 4,909,781 | 3/1990 | Husted. | |
| 5,030,201 | 7/1991 | Palestrant. | |
| 5,057,107 | 10/1991 | Parins et al. | |
| 5,071,424 | 12/1991 | Reger. | |
| 5,074,871 | 12/1991 | Groshong. | |
| 5,080,660 | 1/1992 | Buelna. | |
| 5,163,938 | 11/1992 | Kambara et al. | |

FOREIGN PATENT DOCUMENTS

| | | | |
|---|---|---|---|
| 2275226 | 5/1974 | France | 606/47 |
| 1235497 | 6/1986 | U.S.S.R. | 606/47 |
| 1355266 | 11/1987 | U.S.S.R. | 606/47 |
| 9220291 | 11/1992 | WIPO | 606/47 |

*Primary Examiner*—Lee S. Cohen
*Attorney, Agent, or Firm*—Peter C. Richardson; Lawrence C. Akers; Mark Dryer

[57] ABSTRACT

An apparatus for electrosurgical incision of a stricture within or adjacent to a body lumen, which comprises an electrically conducting, deflectable wire associated with an introducer for introducing the apparatus into the body lumen, wherein a proximal portion of the wire is deflectable outwardly relative to the introducer, and a source of RF electric current connected to the wire whereby RF electric current may be transmitted through the wire when it is in the deflected position.

10 Claims, 5 Drawing Sheets

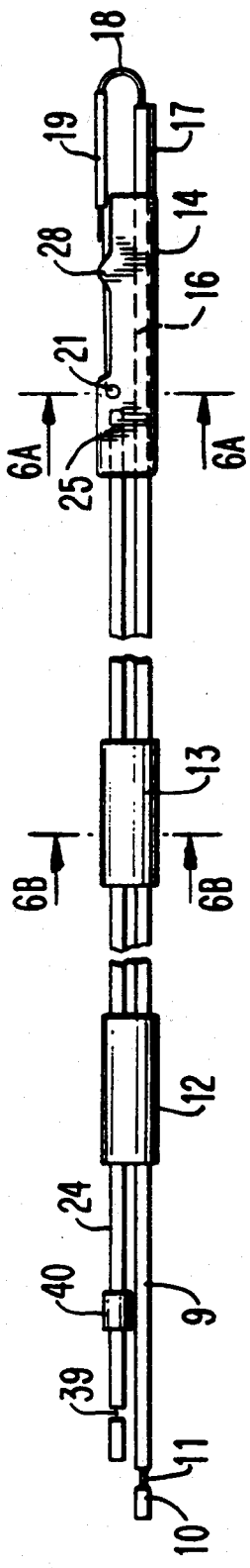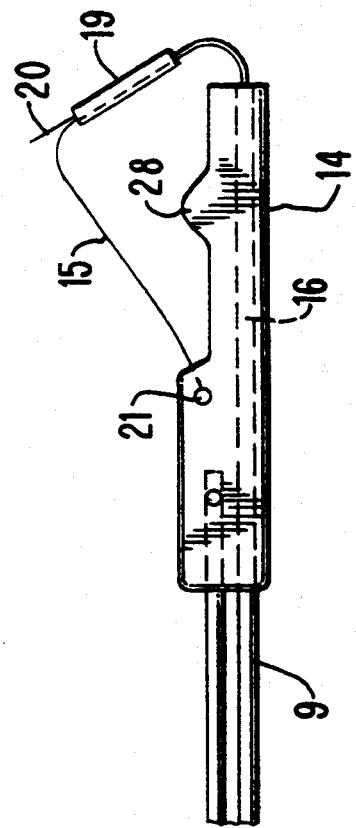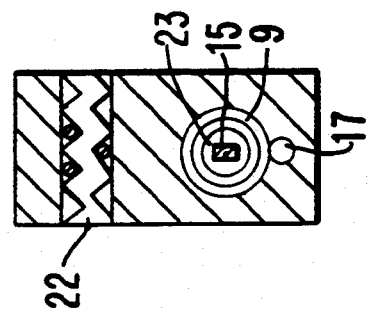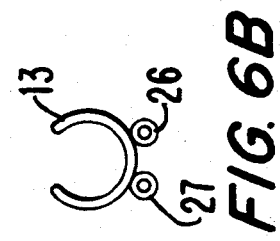

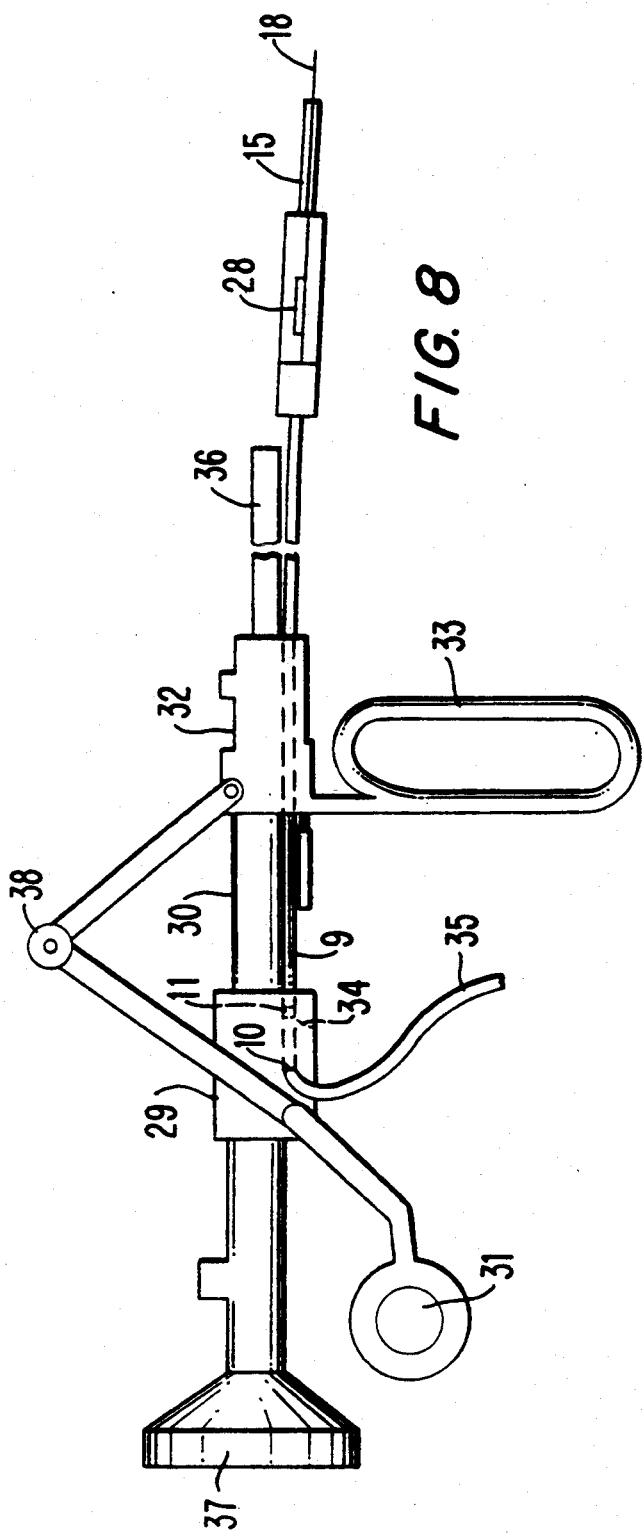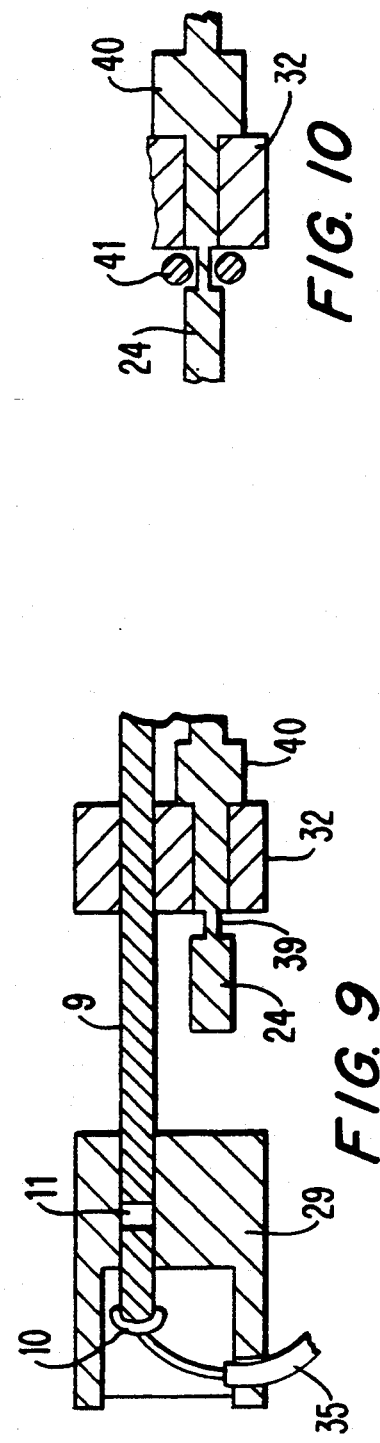

ELECTROSURGICAL APPARATUS

FIELD OF THE INVENTION

This invention relates to an electrosurgical apparatus. More particularly, the invention relates to an electrosurgical knife for transurethral incision of the prostate (TUIP), and to a method for performing TUIP using RF electric energy.

BACKGROUND OF THE INVENTION

Various instruments for performing surgical cutting operations in body lumens, for example, blood vessels, are known in the art.

For example, U.S. Pat. No. 4,909,781 discloses a flexible catheter for opening obstructions in a blood vessel including an annular, rotatable cutter having a flexible coil spring body positioned at one end of a thin, flexible, cylindrical tube adapted for insertion in the vessel.

U.S. Pat. No. 5,030,201 discloses an expandable atherectomy catheter device having an expandable cutting head consisting of deformable cutting members to remove an atheroma or blood clot from a blood vessel.

U.S. Pat. No. 5,071,424 discloses a catheter atherotome comprising a plurality of elongate cutting blades disposed within a catheter for removing plaque from the interior wall of an artery.

U.S. Pat. No. 5,074,871 discloses another form of catheter atherotome having an expansable cutter head at the distal end of a catheter.

All of the above instruments utilize mechanical cutters to remove obstructions in blood vessels.

It is also known to remove obstructions by electrosurgery, i.e., by the use of an electrode, which may or may not be in the form of a sharp blade, which conducts RF electrical energy.

Thus, U.S. Pat. No. 5,057,107 discloses a RF ablation catheter for removing athero-stenotic lesions in blood vessels including a pair of electrodes which create an electric arc for effecting cutting upon application of RF voltage.

U.S. Pat. No. 5,080,660 discloses an electrosurgical electrode having a conductor from which a RF electrical signal is generated, which conductor is surrounded by a sheath having a longitudinal slit to expose the conductor over the region where a surgical procedure is desired.

U.S. Pat. No. 5,163,938 discloses a high-frequency electrosurgical treating device comprising a wire for high-frequency incision in combination with an endoscope. The device is typically used for papillo-sphincterotomy.

The present invention is predicated upon the concept of using an electrosurgical device to perform an incision procedure on the prostate.

Transurethral incision of the prostate (TUIP) is a less traumatic procedure than transurethral resection of the prostate (TURP), the most common operation for benign prostate hyperplasia (BPH). For selected patients TUIP has been found by some urologists to be as effective as TURP, with the advantage that it permits a shorter hospital stay and is associated with fewer complications and undesirable effects.

TUIP is typically performed with a cold (unpowered) knife. It has now been found that the use of an electroctrosurgical (ES) knife, particularly a monopolar electrosurgical knife, powered by radio-frequency (RF) electrical energy from an electrosurgical unit (ESU) makes a cutting operation easier, more direct, and thus less traumatic, than cutting with an unpowered knife. Moreover, use of a RF powered knife permits the convenient application of coagulating power for hemostasis.

However, conventional ES knives are not well adapted for TUIP. The urethra is an elongated, narrow tube about one centimeter in diameter, and the prostate extends radially outward from the urethra and needs to be incised to a depth of up to four centimeters. Accordingly, the instrument should have a configuration with a low profile for atraumatic passage through the urethra, but be adapted to be redeployed into a configuration appropriate for the TUIP procedure. An instrument which satisfies these requirements and also has other advantages is provided by the present invention.

SUMMARY OF THE INVENTION

In accordance with the present invention there is provided an apparatus for electrosurgical incision of a stricture within or adjacent to a body lumen which apparatus is elongated, has a longitudinal axis and comprises an electrically conducting deflectable wire associated with introducer means for introducing the apparatus into the body lumen, means for deflecting a proximal portion of the wire outwardly relative to said introducer means, a source of RF electric current connected to the wire and means for transmitting RF electric current through the wire when it is in the deflected position.

As used herein the term "proximal" means the location at or near the site of the surgical procedure and the term "distal" means the location at or near the operator.

In a preferred embodiment of the invention the introducer means is sized to be inserted in a urethra and the deflectable wire, when deflected, is sized to perform transurethral incision of the prostate or urethral strictures. Alternatively, the apparatus may be sized to be inserted in a ureter to perform incision of a ureteral stricture.

The proximal portion of the apparatus has a low profile, which means that it has a configuration which is elongated and narrow enough to pass through a chosen body lumen without undue trauma or dilation. The apparatus may be substantially rigid or flexible and preferably the proximal end thereof is smooth and rounded to facilitate passage through the body lumen, for example, the urethra or ureter.

Preferably, the introducer means comprises a nosepiece defining a conduit embracing at least part of a proximal portion of the deflectable wire, the wire being slidable within the conduit. The nosepiece preferably is made from an electrically insulating material, for example a moulded biologically compatible plastic, such as a polyurethane.

Preferably the portion of wire deflected outwardly is in the form of a loop defining a monopolar electrosurgical knife, which loop terminates in two distal ends extending beyond the distal end of the introducer means and the means for deflecting the wire is by pulling one distal end and pushing the other distal end. In one embodiment the distal ends of the wire are attached to a reel and the pulling and pushing is effected by rotating the wheel. Also, the wire may be springwound to achieve axial stability (pushability).

In a particularly preferred embodiment the wire is flat so that when it is deflected outwardly it bows in a predictable direction. This provides better directional stability.

The wire is preferably made from a superelastic alloy, especially an alloy of nickel and titanium. Preferably, the deflected position is attained by deflecting the wire loop outwardly in a direction transverse to the longitudinal axis of the apparatus, and the apparatus may include means for controlling the degree of deflection of the wire loop.

Also the loop may include a pointed member, for example a needle, the combination of loop and needle defining a monopolar electrosurgical knife.

In a particularly preferred embodiment of the invention the catheter is accommodated within a cystourethroscope or a small flexible urethroscope so that the apparatus may be used under endoscopic vision. The urethroscope may be a conventional resectoscope.

When the apparatus is sized to perform incision of ureteral strictures it may be accommodated within a ureteroscope.

The invention also provides a method for performing transurethral incision of the prostate of a patient or incision of a ureteral stricture in a patient which comprises inserting an apparatus as described above in the urethra or ureter of the patient until the deflectable wire is located in a position to perform the desired incision, deflecting the wire outwardly to assume a cutting configuration, applying RF electric current through the wire while moving the apparatus to perform the desired incision, switching off the current when the incision procedure is completed, retracting the wire within the apparatus and withdrawing the apparatus from the urethra or ureter.

DETAILED DESCRIPTION OF THE INVENTION

The apparatus according to the invention has an initial low profile configuration which enables it to be inserted into and passed along a body lumen, for example a urethra or ureter, with the minimum discomfort and trauma. This makes it particularly suitable for the performance of TUIP or for the incision of strictures in the urethra or ureter. The invention will be more particularly described with reference to the preferred use as an electrosurgical knife for the performance of TUIP.

A problem associated with prior instruments for TUIP arises from the fact that they are usually inserted through a channel of a rigid cystourethroscope. The size and rigidity of such an instrument makes the procedure painful. The apparatus of the present invention is sized to be used advantageously with a small flexible urethroscope, thereby reducing anesthesia requirements to topical or regional anesthetic agents and consequently reducing the need for support facilities, lengthy hospital confinement and cost. Of course, this does not mean that the greater stability provided by a rigid cystourethroscope need be totally discarded, and in one of the embodiments described herein a rigid resectoscope is used.

The apparatus of the present invention is adapted to perform TUIP with monopolar electrosurgical power. The wire which conveys RF electric current and defines the active electrode or electrosurgical knife is associated with introducer means so that the combination of active electrode and introducer provides a flexible or rigid elongated instrument sized to be inserted into a patient's urethra with minimum trauma or discomfort. During insertion the wire is contained within an appropriate low profile envelope, for example, a nosepiece as hereinafter described. When the apparatus is inserted into a patient's urethra and the operator is ready to perform the incision procedure a control mechanism is activated to deflect the wire, i.e., to cause the cutting electrode to assume its operating configuration. The activation may be accomplished in any one of several ways, for example:(i)

(i) a control wire that is pulled to cause the deflectable wire (electrode) to bow outward;

(ii) two control wires that, when one is pushed and the other pulled, cause the electrode to deflect outwardly from the side of the nosepiece;

(iii) either of the above associated with a reel that, when rotated, pushes and/or pulls the control wire or wires;

(iv) an elastic or superelastic electrode that is contained within a tubular envelope for deployment and bends upward at the proximal end when it is advanced out of the tube; and (v) the electrode carried on an elastic or superelastic non-conducting substrate contained within a tubular sheath for deployment which bends upward at the proximal end when advanced out of the tube and the electrode assumes the same shape as the bent substrate.

When the apparatus of the invention is used as a monopolar electrosurgical knife, the deflectable wire acts as the active electrode when activated by RF electrical current and the circuit is completed by a return electrode attached to the patient's body in a manner known in the art.

BRIEF DESCRIPTION OF THE DRAWINGS

Preferred embodiments of the invention are illustrated in the accompanying drawings, in which:

FIG. 6 is a side elevation of a preferred embodiment of the invention showing the wire in the insertion-withdrawal configuration;

FIG. 6A is a cross section through line A—A of FIG. 6;

FIG. 6B is a cross section through line B—B of FIG. 6;

FIG. 7 is an enlarged side elevation of the proximal end portion of the embodiment of FIG. 6 showing the wire in the operational (cutting) configuration;

FIG. 8 is a side elevation of an apparatus according to the invention mounted in a common type of resectoscope;

FIG. 9 is an enlarged view of a portion of the embodiment of FIG. 8 showing the configuration where the wire is longitudinally movable;

FIG. 10 shows the configuration where the wire is secured;

DETAILED DESCRIPTION OF THE DRAWINGS

Figure 1:
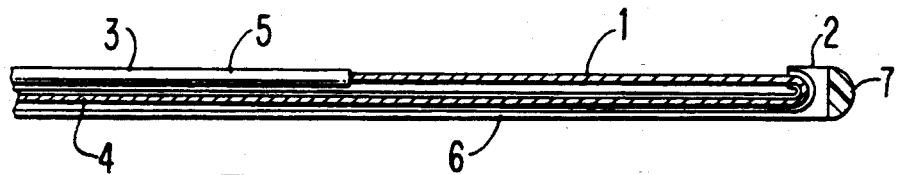
FIG. 1 is a side elevation of a simple embodiment of the invention.
Figure 2:
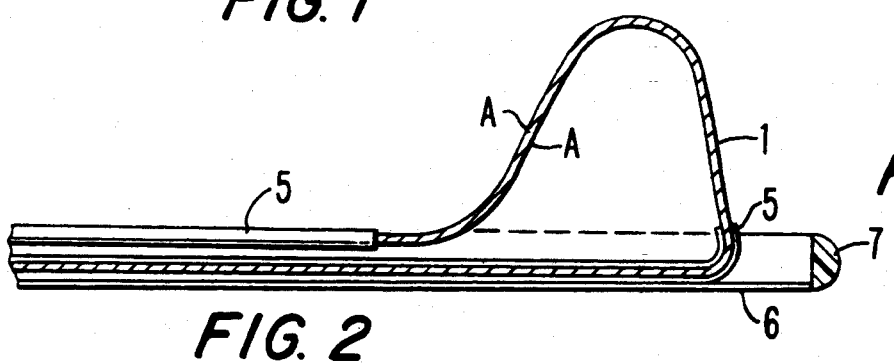
FIG. 2 is a side elevation of the embodiment of FIG. 1 showing the wire in the cutting configuration.

FIG. 1 and FIG. 2 illustrate the proximal portion of an apparatus comprising a deflectable electrically conducting wire 1 which defines a loop 2 at the proximal end of the apparatus and two limbs 3,4 extending toward the distal end of the apparatus. For most of its length the wire has an electrically insulating coating or sheath 5, and only the portion to be deflected and form the cutting electrode is exposed. The proximal portion of the wire is enveloped in a sheath 6, preferably made of a smooth, biocompatible plastic, preferably a polyurethane or polyethylene, having a rounded smooth proximal end 7, which sheath acts as an introducer when the wire is undeflected and contained therein (FIG. 1). The introducer is elongated and has a longitudinal axis and a slot adjacent the proximal end through which the wire may be deflected outwardly in a direction transverse to the longitudinal axis to provide the cutting configuration (FIG. 2).

Figure 2A:
FIG. 2A is an enlarged perspective view (not to scale) of a small portion of the wire at profile A—A of FIG. 2.

As illustrated in FIG. 1, the introducer has a low profile which enables the apparatus to be inserted in a body lumen, for example a urethra or ureter, with minimum trauma. When the apparatus is properly positioned within the urethra, the distal end 4 of the wire is pulled to deflect the exposed proximal portion of the wire outwardly in a direction transverse to the longitudinal axis of the apparatus as shown in FIG. 2. In this embodiment the limb 3 remains fixed. In the preferred embodiment where the wire is flat, as shown in FIG. 2A, the wire bows outwardly without kinking or distortion.

Figure 3:
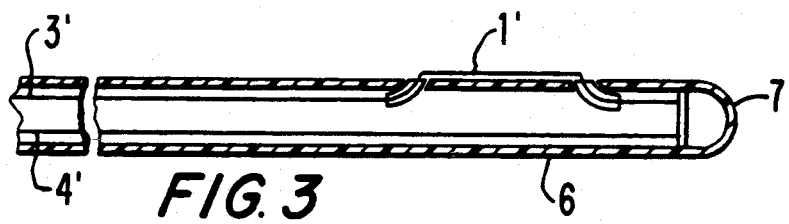
FIG. 3 is a schematic side elevation of another embodiment of the invention.
Figure 4:
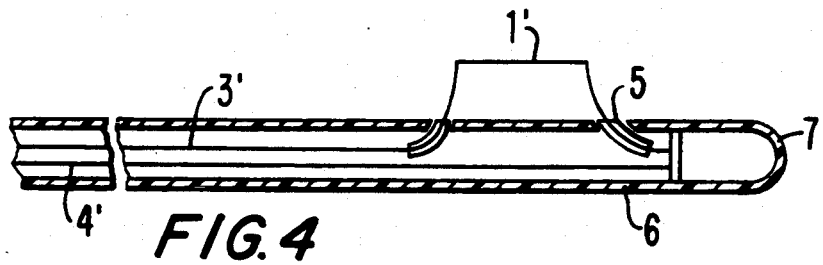
FIG. 4 is a side elevation of the embodiment of FIG. 3 showing the wire in the cutting configuration.
Figure 5:
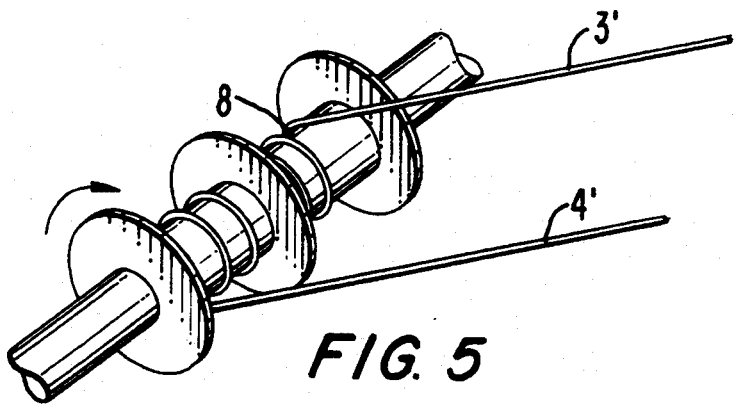
FIG. 5 is an enlarged perspective view of a reel mechanism for deflecting the electrode wire of the embodiment of FIG. 3.

FIG. 3 and FIG. 4 illustrate another embodiment, similar in many respects to the embodiment of FIG. 1 but wherein the distal ends 3' and 4' are both movable to deflect the electrode wire 1 and the desired deflection of the wire is achieved by pushing the distal end 3' and pulling the distal end 4'. In a preferred embodiment, illustrated in FIG. 5, the distal ends of the wire 3', 4' are attached to a reel 8. One of the ends 3' is wound around the core of the reel in a counterclockwise direction and the other end 4' is wound around the core in a clockwise direction. Thus, when the reel is rotated in a clockwise direction, as indicated by the arrow, the wire 4' is pulled and the wire 3' is pushed, whereby the proximal end of the wire is deflected outwardly. When the reel is rotated counterclockwise the wires are moved in the opposite direction and the wire is returned to the withdrawal configuration.

In the apparatus illustrated in FIGS. 1, 2, 3, 4 and 5 the deflected wire is the active electrode in a monopolar electrosurgical cutting knife. The knife is activated by RF electrical current from a standard electrosurgical unit (ESU) connected to the distal end of the wire in a conventional way (connection not shown). The circuit is completed through a return electrode attached to the body of the patient in a conventional manner (not shown).

FIG. 6 and FIG. 7 illustrate a preferred embodiment, particularly suitable for TUIP. FIG. 6 shows the instrument in the insertion-withdrawal configuration and FIG. 7 shows the wire deflected in the cutting configuration. The instrument is adapted to be held in the working element of a resectoscope as described hereinafter with reference to FIG. 8.

The TUIP instrument illustrated in FIG. 6 comprises a conductor-carrying tube 9 (identified herein for convenience only as the "hot tube"), which tube contains a flat profile deflectable wire 15 capable of carrying RF electrical current. RF current from an electrosurgical unit (ESU), not shown, enters the hot tube through a contact 1 0, which is insulated from the exterior of the tube. A notch 11 adjacent the distal end of the tube enables the tube to be held in the working element of a resectoscope and the tube is aligned to the axis of the resectoscope by guides 12 and 13.

The proximal end of the hot tube is associated with introducer means which includes a nosepiece 14 defining a conduit 16 through which the hot tube passes. The nosepiece is made from an electrically insulating polymer, preferably a moulded polyurethane. The diameter of the conduit determines the friction between the hot tube and the nosepiece and thus controls the ease with which the hot tube may slide axially. The sliding motion is what raises and lowers the cutting electrode. A small key 17 prevents rotation of the hot tube within the nosepiece.

The hot tube extends proximally beyond the nosepiece about 0.7 Inch. The insulated cutting electrode wire 18 emerges from the end of the hot tube and makes a hairpin bend before passing through a backing tube 19. A pointed member, preferably a needle 20, extends about 0.1 Inch from the proximal end of the backing tube. The outside of the backing tube is insulated, but the needle is uninsulated and forms part of the cutting electrode. The uninsulated electrode wire 15 with the needle emerges from the proximal end of the backing tube and continues, in a deflected configuration (FIG. 7), to an anchoring point 21 on the nosepiece. The wire is anchored by being passed around a screw 22 within the nosepiece, as shown in FIG. 6A. When the desired length of wire has been taken up the screw is heated to its softening point. As the screw cools it bonds to the nosepiece and attachment of the wire is secured. FIG. 6A also shows hot tube 9, electrode wire 15 with its insulation 23, and key 17. Preferably the electrode wire is high temper 304 stainless steel ribbon wire, insulated by polytetrafluoroethylene shrink tubing. Preferably, the hot tube, cold rod 24, telescope guides 12, 13, backing tube 19, and needle 20 are made from 304 stainless steel.

The cold rod or push rod 24 is the means for holding the nosepiece immobile when changing the configuration of the cutting assembly and it may be a hollow tube or a solid rod. The proximal end of the cold rod is inserted into a hole in the nosepiece and is rigidly attached by a transverse pin 25. Thus, motion of the hot tube 9 relative to the cold rod 24 changes the configuration of the cutting assembly. If the cold rod and hot tube are moved together, the entire instrument moves axially without changing its configuration. The guides 12 and 13 are rigidly attached to the cold rod by attachments 26, but slidably attached to the hot tube by attachments 27 (FIG. 6B).

A notch 39 adjacent the distal end of the cold rod is adapted to accept a clip 41 (FIG. 10) to prevent movement of the cold rod in a proximal direction. A collar 40 welded to the cold rod acts as a stop in the distal direction (FIG. 9).

When the hot tube is pulled in a distal direction while the nosepiece is held immobile the distance the hot tube extends out of the nosepiece is decreased, leaving a shorter distance between the wire's emergence from the tube and its anchoring point. The cutting assembly comprising uninsulated portion 15 of the electrode wire and the part of the needle 20 that extends from the backing tube 19, therefore assumes the cutting configuration as shown in FIG. 7. When the hot tube is pushed in a proximal direction the electrode wire is stretched out and resumes the insertion-withdrawal configuration shown in FIG. 6. A flange 28 near the proximal end of the nosepiece is provided to keep the portion of the instrument near the needle 20 away from the wall of a delivery sheath described hereinafter with reference to FIG. 11.

The mounting of a TUIP instrument according to the invention in a common type of resectoscope is illustrated in FIG. 8. The operation of the working element of the resectoscope involves motion of a distal piece 29, which slides along a tube 30 in response to a manual force exerted at thumb loop 31. A proximal piece 32 of the working element is held stationary by manual force exerted on a finger loop 33. The hot tube 9 of the TUIP instrument is securely held within the distal piece 29 by a knife edge 34 which engages the notch 11 and is supplied, through contact 10, with RF electrical current from the ESU via cable 35. A telescope 36, used for viewing the interior of the urethra and bladder through eyepiece 37 is immobile with respect to proximal piece 32. The motion of the working element is assisted by a spring loaded pivot 38.

FIG. 9 and FIG. 10 illustrate the operation of the system. The hot tube 9 and cold rod 24 slide freely through conduits in proximal piece 32. The hot tube 9 is attached to the distal piece 29 by the knife edge 34 which engages the notch 11, and receives RF current through contact 10. Motion of the distal piece will cause corresponding motion of the hot tube. In the situation shown in FIG. 9, this motion will cause axial motion of the entire TUIP instrument, because friction between the hot tube and the nosepiece is sufficient to prevent change in the configuration of the instrument. However, in the situation shown in FIG. 10, a clip 41 is placed in notch 39. Since the clip is too large to pass through the conduit in proximal piece 32, the cold rod can not move in a proximal direction. Since the collar 40, welded to the cold rod, prevents the cold rod from moving in a distal direction, the cold rod is immobile with respect to proximal piece 32. In this situation the nosepiece is similarly immobile with respect to proximal piece 32. Accordingly, motion of distal piece 29 in a proximal direction has the effect of moving the cutting assembly to the insertion-withdrawal configuration, while motion of the distal piece in a distal direction moves the cutting assembly to the cutting configuration. Thus, with clip 41 in place, movement of the distal piece changes the configuration of the TUIP instrument, while without the clip, movement of the distal piece moves the entire instrument axially without changing the configuration.

Figure 11:
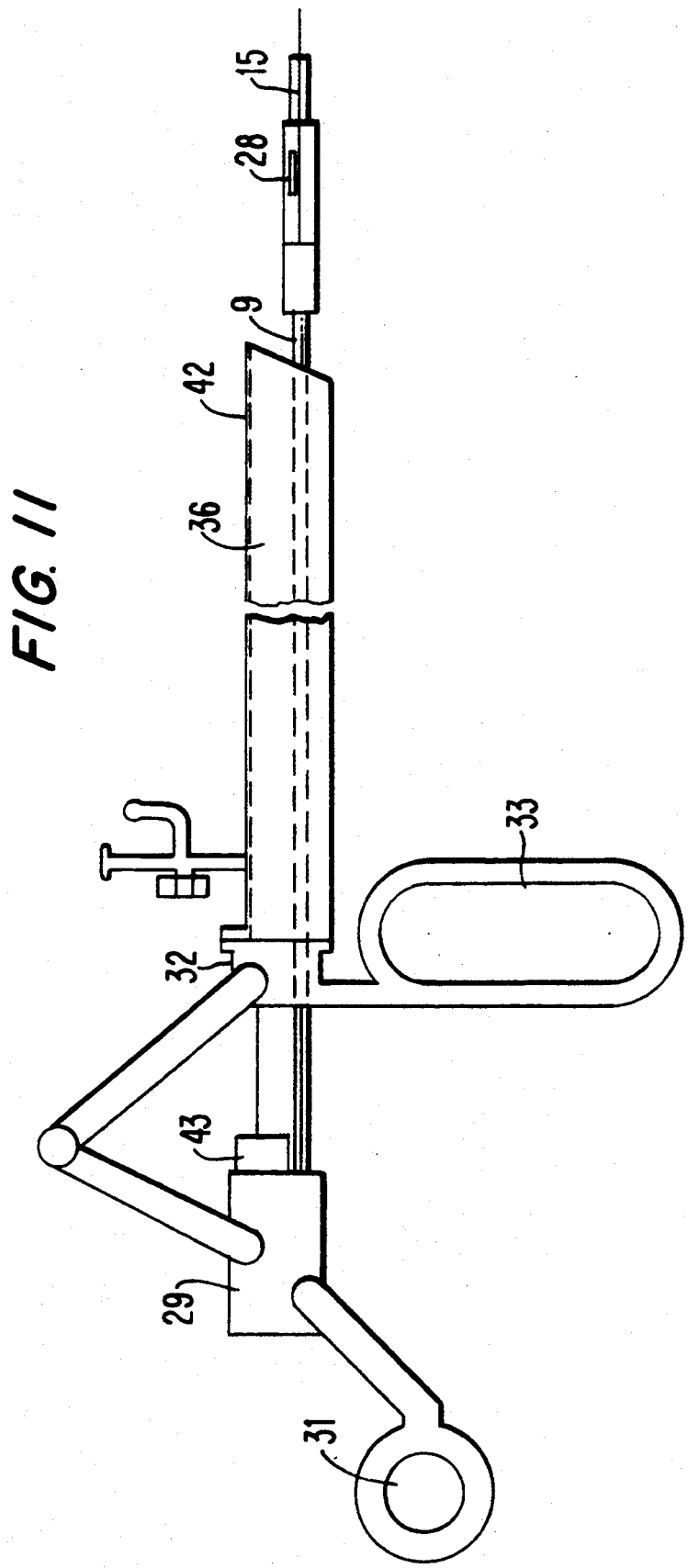
FIG. 11 is a side elevation of an apparatus in the operational mode.
Figure 12A:
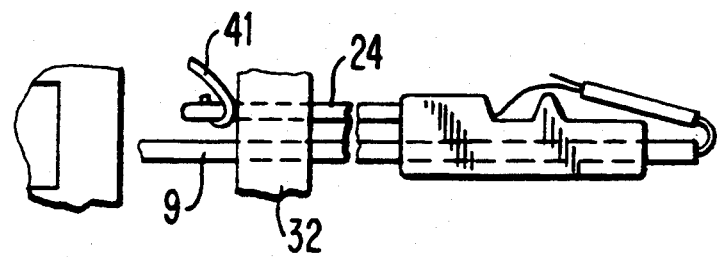
FIG. 12 illustrates four positions:- A, B, C and D, of the apparatus of FIG. 11 during the operational procedure.
Figure 12B:
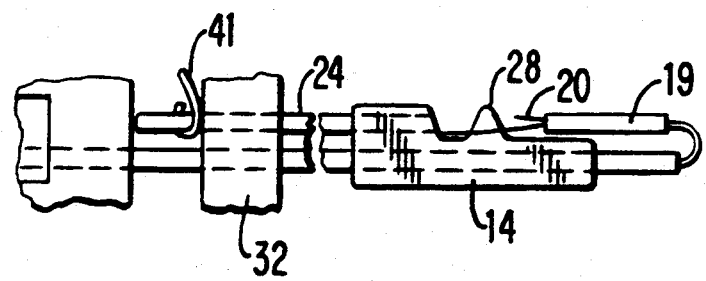

A preferred assembly containing the TUIP instrument for a surgical procedure is illustrated in FIG. 11. The operating surgeon inserts a metal sheath 42 in a patient's urethra. A spacer 43 may be attached to the distal piece of the working element to limit its travel, which has the effect, as described hereinafter, of allowing the surgeon to raise the cutting assembly to any desired height less than or equal to the maximum. The sheath 42 is a hollow tube with a lumen having a diameter large enough to accommodate the viewing telescope and the TUIP instrument. Initially, a viewing telescope is passed through the sheath to permit inspection of the urethra, prostate and bladder. When the surgeon is ready, the proximal piece 32 of the resectoscope's working element is attached to the sheath. As shown in FIG. 9, both the cold rod 24 and the hot tube 9 are passed through conduits in the proximal piece 32. Clip 41 is placed within the notch 39 of the cold rod. The instrument is typically in the relaxed position shown in FIG. 12A. This position minimizes strain on the instrument during storage, but is not adapted either for insertion-withdrawal or for surgery. In the next step the distal piece 29 is moved forward so that the knife edge 34 engages the notch 11 of the hot tube 9. In this position, the hot tube can receive RF current through contact 10. As shown in FIG. 12B, distal piece 29 is then moved as far as possible in the proximal direction, thus moving the cutting assembly to the insertion-withdrawal configuration. This is the configuration in which the tuip instrument has the lowest profile and therefore passes most easily through sheath 42. The instrument may be passed through the sheath 42 to the prostatic urethra.

Figure 12C:
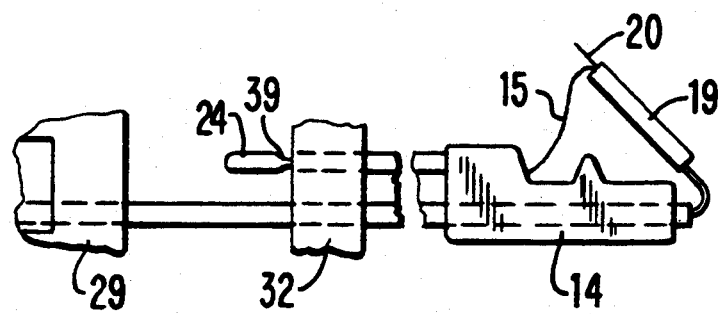

To perform incision of the prostate, the surgeon moves the cutting assembly to the cutting configuration by drawing back the distal piece 29 by means of manual force at thumb loop 31. The cutting configuration is shown in FIG. 12C. The surgeon then advances the elevated cutting assembly to its most proximal position by pushing forward on thumb loop 31. A commercially available ESU supplies RF current to the hot tube 9 through cable 35 and contact 10. In a typical operation, the esu would provide about 140 watts power at a potential of about 200 volts and a frequency of about 750 kilohertz to drive a current of about 0.7 Ampere. To perform the incision, the surgeon moves the electrode wire through tissue in a distal direction by drawing back on thumb loop 31 while applying RF current from the ESU. The needle 20, acts as a hook to facilitate attachment and movement of the cutting edge through the tissue. Since the clip 41 has been removed, the entire instrument moves as a unit as described above. Typically the application of power is controlled by a footswitch operated by the surgeon, and power is applied only when the instrument is being moved in a distal direction.

Figure 12D:
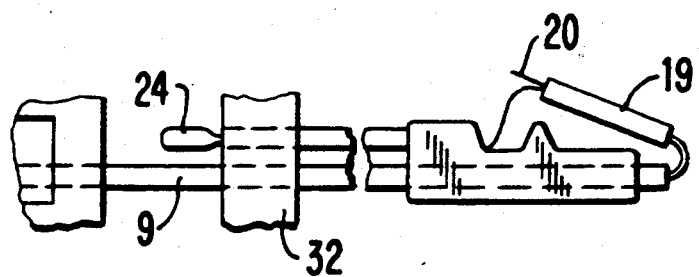

In a preferred embodiment means is provided for controlling the degree of deflection of the wire loop. Thus, use of the spacer 43, as shown in FIG. 11, decreases the distance by which the distal piece 29 may be drawn back, with the result, shown in FIG. 12D, that the cutting assembly is elevated to a height less than that achieved without the spacer. This is useful if an incision of smaller depth is desired. The instrument will normally be supplied with several marked spacers of different thicknesses for achieving various heights as desired by the surgeon.

When the desired incision is made, the thumb loop is again drawn back as far as possible, and the clip 41 is placed in the notch 39. The thumb loop is then moved in the proximal direction as far as it will go, causing the cutting assembly to assume the insertion-withdrawal configuration. The instrument is then withdrawn from the sheath. The flange 28 pushes the part of the instrument nearest the needle 20 away from the wall of the sheath, thus avoiding the danger that the needle will snag the sheath and prevent smooth withdrawal of the instrument.

The use of an apparatus according to the invention in a procedure as described herein provides a safe and efficacious way of performing a TUIP operation or incision of a ureteral stricture.

We claim:

1. An apparatus for electrosurgical incision of a stricture within or adjacent to a body lumen, which apparatus comprises introducer means which is elongated and has a distal end, a proximal end and a longitudinal axis, an electrically conducting, deflectable wire associated with the introducer means for introducing the wire into the body lumen, means for deflecting a proximal portion of the wire outwardly relative to the introducer means; wherein the introducer means comprises a cold rod, a nosepiece attached to the cold rod, which nosepiece defines a conduit embracing at least part of a proximal portion of the deflectable wire, the wire being slidable within said conduit, the portion of wire deflected outwardly is in the form of a loop defining a monopolar electrosurgical knife, which loop terminates in two distal ends, a first end being anchored to an anchoring point on the nosepiece and a second end defining a hot tube extending beyond the distal end of the introducer means, and the means for deflecting the wire is by pulling the hot tube and pushing the cold rod; a source of RF electric current connected to the wire and means for transmitting RF electric current through the wire when it is in the deflected position.

2. An apparatus according to claim 1, in which the introducer means is sized to be inserted in a urethra and adjacent to a prostate, and the deflectable wire, when deflected, is sized to perform transurethral incision of the prostate or urethral strictures.

3. An apparatus according to claim 1, in which the introducer means is sized to be inserted in a ureter and the deflectable wire, when deflected, is sized to perform incision of ureteral strictures.

4. An apparatus according to claim 1, in which the wire is made from a superelastic alloy.

5. An apparatus according to claim 4, in which the alloy is an alloy of nickel and titanium.

6. An apparatus according to claim 1 which includes a spacer for controlling the degree of deflection of the wire loop, which spacer is positioned adjacent the distal end of the introducer means.

7. An apparatus according to claim 1, which includes a backing tube having a proximal end and a distal end surrounding the deflectable wire and a pointed member extending from the proximal end of the backing tube, the combination of loop and pointed member defining a monopolar electrosurgical knife.

8. An assembly comprising apparatus according to claim 2 in combination with a conventional resectoscope having working elements in which the apparatus is operatively connected to the resectoscope such that said working elements also operate to deflect the wire.

9. A method for performing transurethral incision of the prostate of a patient which comprises inserting an apparatus according to claim 2 in the urethra of the patient until the deflectable wire is located in a position to perform the desired incision, deflecting the wire outwardly to assume a cutting configuration, applying RF electric current through the wire while moving the apparatus to perform the desired incision, switching off the current when the incision procedure is completed, retracting the wire within the apparatus and withdrawing the apparatus from the urethra.

10. A method for performing incision of a ureteral stricture in a patient which comprises inserting an apparatus according to claim 3 in the ureter of the patient until the deflectable wire is located in a position to perform the desired incision, deflecting the wire outwardly to assume a cutting configuration, applying RF electric current through the wire while moving the apparatus to perform the desired incision, switching off the current when the incision procedure is completed, retracting the wire within the apparatus and withdrawing the apparatus from the ureter.

* * * * *